United States Patent [19]

Combet-Blanc et al.

[11] Patent Number: 6,022,537
[45] Date of Patent: Feb. 8, 2000

[54] BACTERIAL STRAINS OF THE GENUS BACILLUS, CLOSELY PHENOTYPICALLY RELATED TO THE GENUS LACTOBACILLUS, CULTURE METHOD AND USE

[75] Inventors: Yannick Combet-Blanc, Marseilles; Bernard Ollivier, Roquevaire; Jean-Louis Garcia, Aix en Provence, all of France

[73] Assignee: Institut Francais de Recherche Scientifique pour le Developpement en Cooperation (Orstom), Paris, France

[21] Appl. No.: 08/676,141

[22] PCT Filed: Jan. 18, 1995

[86] PCT No.: PCT/FR95/00056

§ 371 Date: Jul. 10, 1996

§ 102(e) Date: Jul. 10, 1996

[87] PCT Pub. No.: WO95/19425

PCT Pub. Date: Jul. 20, 1995

[30] Foreign Application Priority Data

Jan. 18, 1994 [FR] France ................................ 94 00485

[51] Int. Cl.[7] ............................ A01N 63/00; C12P 21/06; C12N 1/12; C12N 1/00

[52] U.S. Cl. .................... 424/93.1; 435/69.1; 435/252.1; 435/853; 435/854; 435/855; 435/856; 435/857

[58] Field of Search ...................................... 435/853, 854, 435/855, 856, 857, 252.1, 69.1; 424/93.1

[56] References Cited

FOREIGN PATENT DOCUMENTS

| 0 113 215 | 7/1984 | European Pat. Off. . |
| 0 298 641 | 1/1989 | European Pat. Off. . |

OTHER PUBLICATIONS

Combet–Blanc et al. International Journal of Systematic Bacteriology 45(1):9–16 (see abstract), Jan. 1995.

Delaporte et al. C.R. Hebd. Seances Acad. Sci., Ser. D. 264(19):2344–6 (see abstract), 1967.

Burgess et al J. Cell Biology 111: 2129–2137, Apr. 1990.

Lazar et al. Mol. Cell Biology 8(3): 1247–52, Mar. 1988.

Wayne et al (Journal of Systematic Bacteriology, vol. 37, No. 4, Oct. 1987, p. 463–464).

*Primary Examiner*—Anthony C. Caputa
*Assistant Examiner*—Mark Navarro
*Attorney, Agent, or Firm*—Nixon & Vanderhye P.C.

[57] ABSTRACT

Bacterial strains of genus Bacillus closely phenotypically related to genus Lactobacillus. The strains are moderately thermophilic, have amylolytic properties and/or are capable of producing L(+) lactate, and are useful for producing metabolites such as L(+) lactate.

13 Claims, 2 Drawing Sheets

10μm 0.2μm

BACTERIAL STRAINS OF THE GENUS BACILLUS, CLOSELY PHENOTYPICALLY RELATED TO THE GENUS LACTOBACILLUS, CULTURE METHOD AND USE

BACKGROUND OF THE INVENTION

1. Field of the Invention

The invention relates to bacterial strains closely phenotypically related to the genus Lactobacillus.

It also relates to methods for culture of these strains and to their industrial uses.

The invention more particularly relates to bacterial strains isolated from palm wine.

2. Description of Related Art

It is known that palm wine is an alcoholic drink originating from spontaneous fermentation of the sap of trees belonging to the palm tree family. This sap comprises about 10 to 15% (w/v) of sucrose, several amino acids and vitamins.

DETAILED DESCRIPTION OF THE INVENTION

Figure 1:
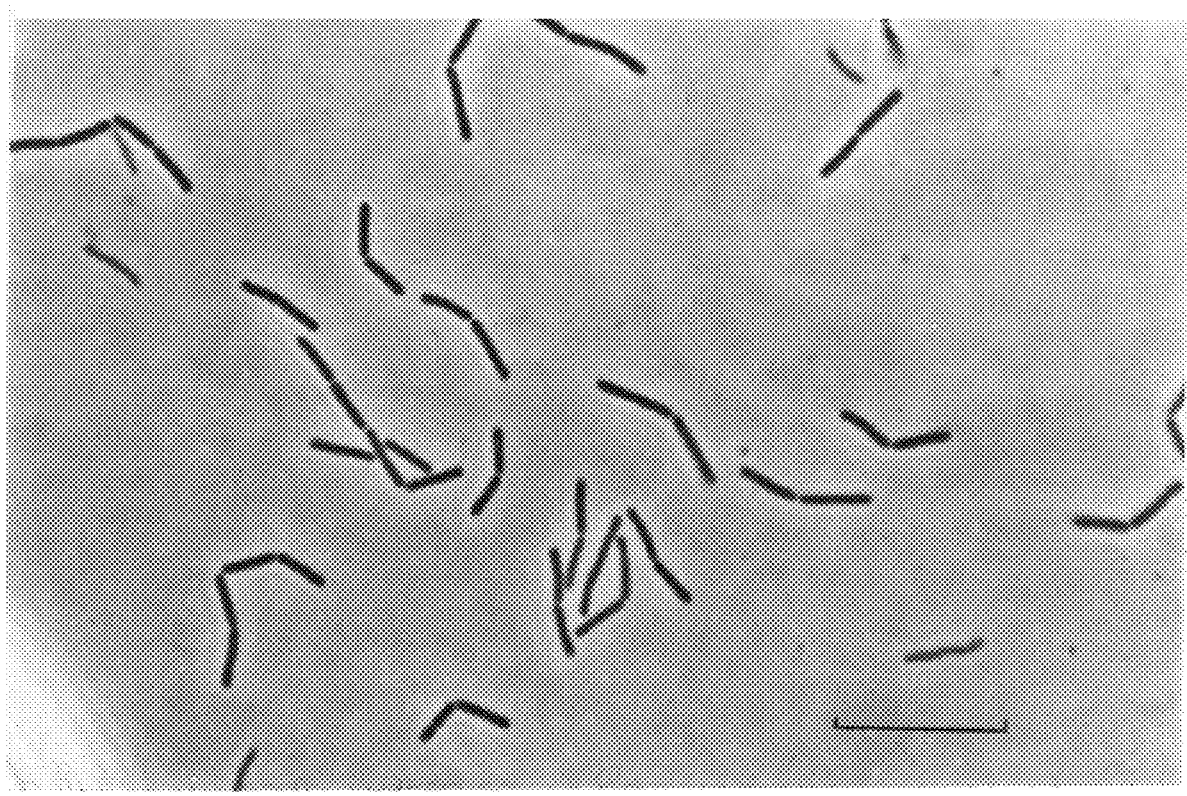
FIG. 1 shows a photograph of cells of the invention under an optical microscope.

Microbiological studies which have been carried out have demonstrated the presence of an abundant mesophilic flora made up of several species of bacteria and yeasts.

A study of the thermophilic anaerobic flora present in a palm wine originating from Senegal by the inventors led them to isolate a strain which is still unidentified and has properties of great advantage in various fields of industry.

The object of the invention is thus to provide new strains of this type.

It also relates to the provision of culture protocols for these strains specifying the physico-chemical conditions and the composition of the culture medium which allow favourable production of cells and/or certain metabolites, such as, for example, L(+)-lactate.

According to another aspect, the invention relates to the direct use of these strains or that of their metabolites in various industries.

The bacterial strains of the invention are characterized in that they have a DNA sequence of which at least part is capable of hybridizing with at least part of the genome or plasmid DNA of the strain deposited at the Collection Nationale de Cultures de Microorganismes (C.N.C.M.= National Collection of Microorganism Cultures) on Nov. 24, 1993 under no. I-1378.

Advantageously, at least 70% of the genome of the strains of the invention is capable of hybridizing with the DNA of the strain deposited.

According to another aspect, these strains are characterized in that they are moderately thermophilic, have amylolytic properties and/or are capable of producing lactate from carbohydrates. It is pointed out that the lactate produced is advantageously L(+)-lactate to the extent of more than 95%.

The expression "moderately thermophilic" is understood as meaning bacterial strains which are capable of growing at temperatures of the order of 25 to 58.5° C., with an optimum between 47 and 53° C.

The invention more particularly relates to strains of the genus Bacillus as demonstrated by comparison of RNA sequences of the 16 S fraction of the ribosomes.

Strains of this type are also characterized in that they are heterolactic, that is to say they are capable of producing compounds other than L(+)-lactate, in particular ethanol, formate and acetate, from carbohydrates, depending on the physico-chemical conditions of the culture medium, in particular depending on the pH and the sugars/peptides ratio.

Such strains are also characterized in that they have no cytochrome and are not capable of utilizing nitrates or sulphates as a terminal electron acceptor.

They have a catalase and their metabolism is facultatively anaerobic.

According to another embodiment of the invention, these strains are characterized by anaerobic growth conditions and microaerophilic properties, that is to say low partial pressures of oxygen stimulate their growth.

Their growth takes place more specifically at a pH of 5.4 to 8.5, with an optimum for growth of about 6.8 to 7.2.

The bacterial strains of the invention are also characterized in that they are Gram-positive.

According to another embodiment of the invention, the bacterial strains are characterized by non-sporulated cells, isolated or in chains of 3 or 4 cells, which are rod-shaped with peritrichous flagella.

According to another embodiment, the content of guanine plus cytosine in the DNA of the bacterial strains of the invention is less than 50 mol%, in particular of the order of 40 mol%.

The invention particularly relates to the bacterial strain deposited at the C.N.C.M. on Nov. 24, 1993 under no. I 1378.

The identification reference of this strain is DKP. *Bacillus thermoamylovorans* gen. nov. sp. nov will be used as the name for taxonomic designation, the previous designation being *Lactobacter thermoamylovorans* gen. nov. sp. nov.

Mutants of the strains corresponding to the above definitions also fall within the context of the invention, since they retain at least 70% of the capacity for hybridization with the DNA of the strain deposited.

In accordance with the invention, the bacterial strains defined above are obtained by culture under anaerobic conditions, or at the very least under a low partial pressure of oxygen, at a pH of about 5.4 to 8.5 in a base medium comprising a sugar which can be used as a source of energy by these strains and peptides as a source of nitrogen, at a temperature of 25 to 58.5° C.

Culture under a low partial pressure of oxygen is understood as meaning culture carried out, for example, in a liquid medium with air above.

The culture is advantageously carried out at a pH of 6.8 to 7.2 and at a temperature of 47 to 53° C.

Under optimum conditions of pH and temperature, the time for doubling of the biomass is about 40 to 45 minutes.

For growth of the strains, carbohydrates, more particularly glucose, as compounds which are a source of carbon and energy, peptides, as a source of nitrogen, and growth factors are chiefly used.

The peptides and the growth factors are present, for example, in yeast extracts and trypsin hydrolysates of casein or gelatin.

The addition of vitamins allows the growth to be accelerated, but is not essential.

It is particularly favourable if a hydrolysate of casein obtained by the action of trypsin, such as that currently called BIOTRYPTASE (Bio Mérieux, Caponne, France, or yeast extracts are added to the culture medium.

The bacterial colonies formed after about 48 h of culture under the conditions given above are taken up individually in liquid medium in order to obtain pure cultures.

Various properties of the strains of the invention have been indicated in the above description. These properties have applications in widely varying fields.

These strains, due to their thermophilic and amylolytic properties, which also manifest themselves in very dilute media, are thus advantageously added to industrial effluents for the purpose of decontamination.

The invention thus relates to a process for the treatment of industrial effluents for the purpose of decontamination, characterized in that it comprises using bacterial strains as defined above.

The phylogenetic proximity of the strains of the invention with species belonging to the genus Bacillus and the physiological similarities with lactobacteria are advantageously utilized in food fermentation processes. Their fermenting and enzymatic properties enable them to advantageously replace and/or to supplement those attributed to lactobacteria and to Bacilli here.

These strains are also of great advantage for the development of mutants by transfer of genetic material between these strains, lactobacteria and Bacilli, which allows a range of properties common to these bacteria to be cumulated.

The moderate thermophilic, facultative anaerobic and neutrophilic characteristics of the strains of the invention are also of great advantage from the aspect of use in a pure culture. In fact, the possibility of culture at a temperature extending to 58.5° C. enables sources of contamination by other microorganisms to be limited, the kinetics of cell metabolism to be accelerated and the solubility of components of the culture medium to be increased. Furthermore, at this temperature the low concentration of dissolved oxygen does not inhibit but stimulates growth of these facultative anaerobic strains, which considerably facilitates the use of cultures, avoiding all the technical constraints associated with anaerobiosis. The neutrophilic character of the strains, which is considerable with respect to the acidophilicity of lactobacteria, enables corrosion problems to be avoided and the life of installations to be prolonged. The capacity of the strains of the invention for fermentation of a wide variety of sugars, in particular starch, lactose and sucrose, is a significant bonus. These three sugars, which can potentially be used as energy substrates, are in fact available in a large quantity in various forms.

The possibility of having an effect on the metabolism of these strains by controlling the physico-chemical parameters of the culture medium (pH, sugars/peptides ratio) widens their field of use. It is thus possible, for example, to direct the fermentation towards production of cells and cell metabolites such as enzymes. It is also possible to direct the energy metabolism of the strain by promoting either production of lactate or production of acetate, ethanol and formate.

The invention therefore also relates to a process for the production of metabolites such as L(+)-lactate, acetate, formate and ethanol, characterized in that it comprises culture of a bacterial strain as defined above under conditions suitable for its development and for the production of the metabolite required, and recovery of the metabolites produced, followed by isolation of the desired metabolite and its purification.

The lactic acid produced by the strains of the invention is of great advantage, since it is made up, to the extent of more than 95%, of L(+)-lactate, which can be assimilated by superior organisms, while D(−)-lactate has a toxicity characteristic.

It is separated off from the culture and concentrated, for example by evaporation, to dryness if appropriate.

The concentrates or dried products are used as such or treated to form the desired derivatives of lactic acid.

It is known that there are very wide uses of lactic acid or its esters and other derivatives.

Thus, lactic acid is used in the agro-alimentary industry by being incorporated into drinks, beers, dairy products, such as cream, cheese or butter, ice-creams or also preserves.

As a surfactant, it will advantageously be used in panification and in Viennese bread in the form, for example, of lactyl mono- and diglycerides and sodium stearyl lactate.

In the pharmaceuticals industry, potassium lactate may constitute a substitute for sodium chloride of particular value in cases of hypertension.

It is also used for its complexing properties, in particular with iron and calcium for treatment of deficiencies.

Finally, among the uses of lactic acid and its salts and derivatives in the chemical industry there may be mentioned its use in the production of plastic resins, adhesives, pesticides, textiles, or also paints, diluents and solvents, or for the treatment of the surface of metals.

Its great advantage in the chemistry of polymers, where it is used to manufacture polylactides and/or copolymers with, for example, polyalkylene oxides, polyvalent alcohols, glycolic acid, hydroxycarboxylic acids, copolymers of ethylene and propylene, butyl rubbers or thermoplastic polyurethane elastomers, may be emphasized. Various articles may be manufactured from these polymers and/or copolymers, in particular for packaging, films for medical uses for production of dressings, or also coating materials for surgical sutures.

The culture medium recommended for industrial use of the strains of the invention for production of L(+)-lactate has the advantage of being lower in cost than that usually used for lactobacteria, taking into account the cost of yeast extract or of corn steep liquor comprising the growth factors essential for these bacteria. In fact, since lactobacteria are very demanding in growth factors, for a good productivity with respect to lactic acid the use of a medium in which the sugar/growth factors ratio is 1 is recommended, whereas for the strains of the invention this ratio should be 2.

Other characteristics and advantages of the invention are mentioned in the description, given by way of example, which follows and which relates to the abovementioned strain, called strain DKP, deposited at the C.N.C.M. under no. I-1378.

Figure 2:
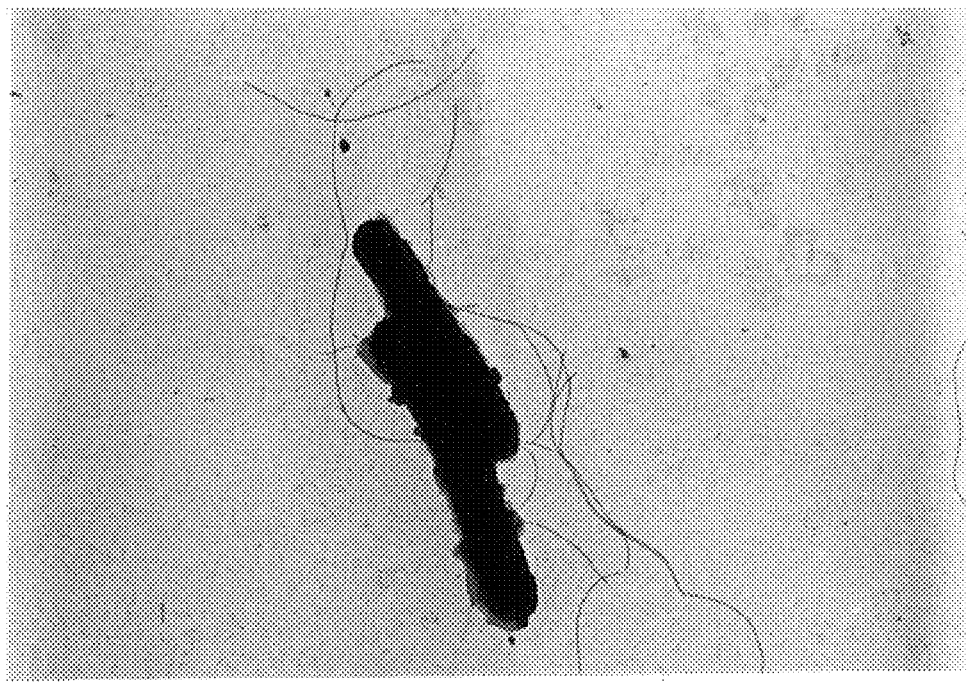
FIG. 2 shows a photograph of cells of the invention under an electron microscope with a magnification of 20,000.
Figure 3:
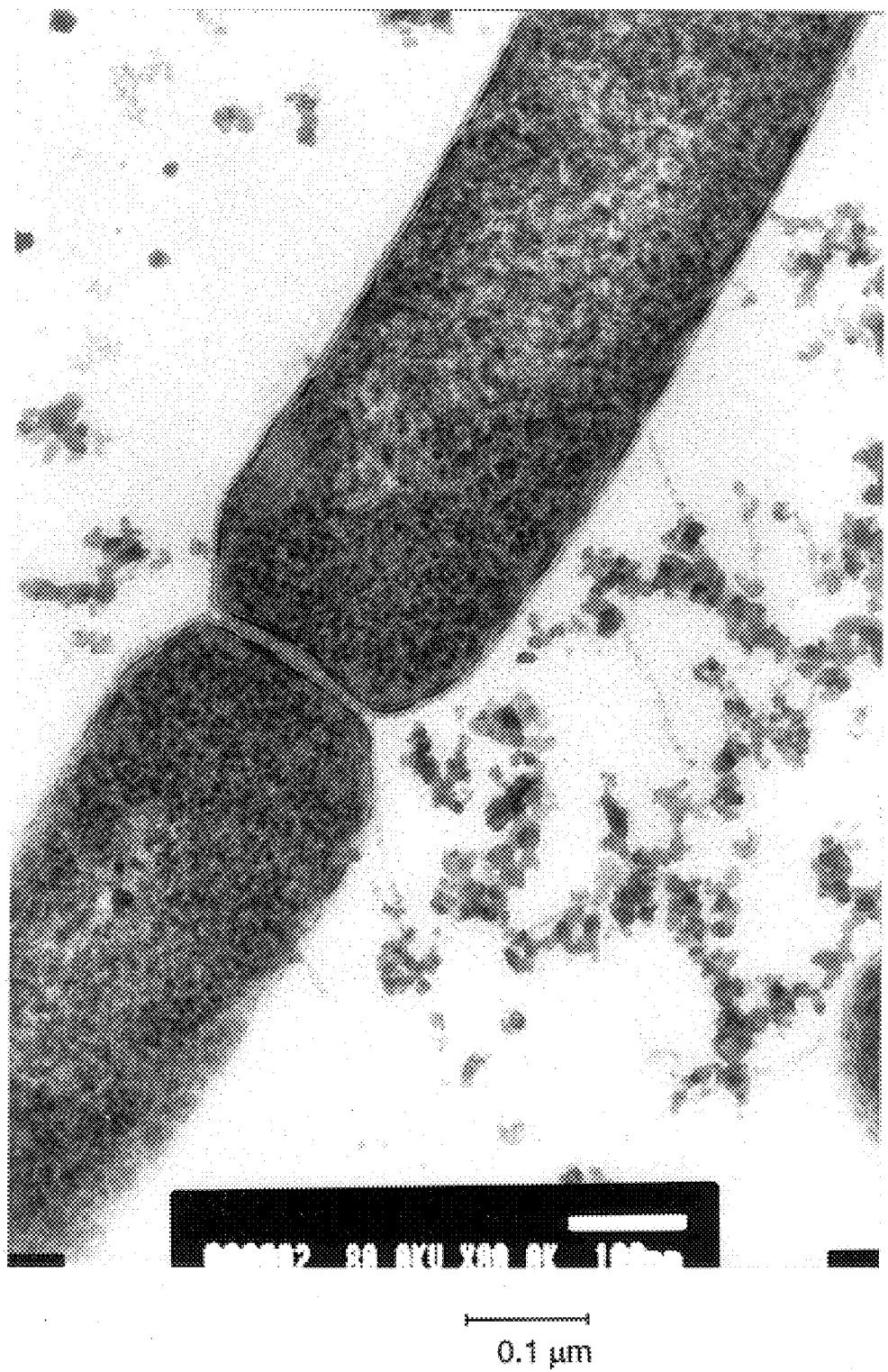
FIG. 3 shows a photograph of cells of the invention under an electron microscope with a magnification of 80,000.

Reference will be made here to FIGS. 1 to 3, which show photographs of cells of this bacteria under an optical microscope (FIG. 1) and under an electron microscope, with a magnification of 20,000 on FIG. 2 and 80,000 on FIG. 3.

a. PROCEDURE FOR ENRICHMENT AND ISOLATION OF THE STRAINS

Culture Media and Methods

The following culture medium is used:

| | |
|---|---|
| Glucose | 10 g |
| Yeast extract | 5 g |
| Biotryptase | 5 g |
| KH$_2$PO$_4$ | 1 g |
| MgCl$_2$.6H$_2$O | 0.4 g |
| NH$_4$Cl | 1 g |
| FeSO$_4$.7H$_2$O | 5 mg |
| Balch mineral solution (below) | 25 ml |
| Balch trace elements solution (below) | 1 ml |
| Tween 80 | 1 ml |
| Distilled H$_2$O, q.s.p. | 1,000 ml |

The compositions of the Balch mineral solution and the Balch trace elements solution are as follows:

| Balch mineral solution | |
|---|---|
| KH$_2$PO$_4$ | 6 g |
| (NH$_4$)$_2$SO$_4$ | 6 g |
| NaCl | 12 g |
| MgSO$_4$.7H$_2$O | 2.6 g |
| CaCl$_2$.2H$_2$O | 0.16 g |
| Distilled water, q.s.p. | 1,000 ml |
| Balch trace elements solution | |
| Nitriloacetic acid | 1.5 g |
| MnSO$_4$.2H$_2$O | 0.5 g |
| MgSO$_4$.7H$_2$O | 3 g |
| NaCl | 1 g |
| FeSO$_4$.7H$_2$O | 0.1 g |
| CoCl$_2$.6H$_2$O | 0.1 g |
| CaCl$_2$.2H$_2$O | 0.1 g |
| ZnCl$_2$ | 0.1 g |
| CuSO$_4$.5H$_2$O | 0.01 g |
| AlK(SO$_4$)$_2$ | 0.01 g |
| H$_3$BO$_3$ | 0.01 g |
| Na$_2$MoO$_4$ | 0.01 g |
| Distilled H$_2$O, q.s.p. | 1,000 ml |

The pH of the culture medium is adjusted to pH 7.5 with 10 M KOH before sterilization.

The medium is then brought to the boiling point and subsequently cooled and distributed, under a stream of nitrogen
- into bottles of the penicillin type or serum bottles in an amount of 20 ml per bottle
- into Hungate tubes in an amount of 10 ml per tube, and
- into Hungate tubes containing 4.5 ml of 3.5% agar medium per tube.

After treatment in an autoclave at 110° C. for 45 minutes, the following are added:
- 1 ml 10% NaHCO$_3$ +0.2 ml 2% Na$_2$S.9H$_2$O into the serum bottles,
- 0.5 ml 10% NaHCO$_3$ +0.1 ml 2% Na$_2$S.9H$_2$O into the Hungate tubes containing 10 ml, and
- 0.25 ml 10% NaHCO$_3$ +0.05 ml 2% Na$_2$S.9H$_2$O into the Hungate tubes containing the agar.

The NaHCO$_3$ and Na$_2$S solutions used are sterile.

The media, which are liquid in the first two cases and solid in the last case, are ready for inoculation.

Enrichment Procedure:

The bottles containing the culture medium prepared anaerobically as defined above and inoculated with samples of palm wine are subjected to incubation at a temperature of 50° C. After several subcultures, the anaerobic and thermophilic flora initially present in the palm wine has become dominant.

Procedure for isolation by the technique of roll tubes by the method of Hungate and Macy (1) and (2):

Preparation of the roll tubes.

The Hungate tubes are heated to 90° C. for the purpose of melting the solid medium. They are then cooled to 50° C., while maintaining the agar in the molten state.

The tubes are inoculated with the final enrichment medium obtained above, in an amount of 0.5 ml in each tube.

The molten agar-agar is distributed, by centrifugation, over the wall of the tube and solidified by cooling.

Isolation

After incubation of the roll tubes for 48 h at 50° C., each colony is resuspended and diluted in cascade in a series of Hungate tubes containing a liquid medium.

The tubes are incubated at 50° C. for 24 hours.

A serum bottle containing liquid medium is then inoculated from the last dilution which shows growth, and the bottle is subjected to incubation at 50° C. for 24 hours.

It is verified under an optical microscope that all the cells are identical.

The isolation procedure is repeated at least once, verifying that all the colonies have identical characteristics.

The resulting culture is pure.

b. DESCRIPTION OF THE STRAIN

Morphological Characteristics

After incubation of the roll tubes for 48 hours, the strain obtained, called strain DKP, is in the form of smooth white colonies with a diameter of 1 to 1.5 mm. The non-sporulated cells, isolated or in a chain of 3 to 4 cells (see photograph 1), are rod-shaped of 0.35 to 0.4 μm diameter and 3 to 4 μm length and have peritrichous flagella (see photograph 2). The cell wall has the characteristics of Gram-positive bacteria (see photograph 3).

Biochemical characteristics and metabolic properties.

Elements of the Medium

Peptides, for example yeast extracts, will advantageously be added to a medium comprising carbohydrates, in particular glucose, as a source of energy, in order to promote growth. No growth is observed if gelatin or casein is used instead of yeast extract. However, a weak growth is found if amino acids are added instead of yeast extract.

Growth conditions and metabolic properties

Growth takes place under anaerobic conditions, or at the very least under a low partial pressure of oxygen. The colonies are not always found on Petri dishes incubated under aerobiosis. The cells have a catalase, but no cytochromes. NO$_3$− and SO$_4$. are not reduced and no production of indole, H$_2$S or H$_2$ is observed. In a medium with arginine as the source of energy, NH$_3$ is produced but no growth is observed.

The pH values for growth are 5.4 to 8.5, with an optimum at 7.0.

The optimum temperature for growth is about 50° C., 58.5° C. being the upper temperature limit.

In a medium comprising yeast extract and glucose as sources of energy, at pH 7.0 and at a temperature of 50° C., the maximum time for doubling of the biomass is 40 to 45 min.

The products of the fermentation of glucose are acetate, ethanol, formate and lactate. The lactate produced is L(+)-lactate to the extent of 96%. The molar proportions of acetate, ethanol and formate are of the order of 1:1:2 respectively, while the proportion of lactate with respect to these three products varies according to the culture conditions (pH and glucose/peptides ratio).

Fermentable Sugars

The following sugars are fermented within 24 hours: L-arabinose, ribose, D-glucose, D-fructose, D-mannose, rhamnose, amygdalin, arbutin, esculin, salicin, cellobiose, maltose, trehalose, starch, glycogen, β-gentiobiose and gluconate.

A slower fermentation of 48 to 96 h is observed with D-xylose, galactose, N-acetyl-D-glucosamine, lactose, sucrose, melezitose and D-turanose.

No fermentation is observed for glycerol, erythritol, D-arabinose, L-xylose, adonitol, L-sorbose, dulcitol, inositol, mannitol, sorbitol, methyl D-mannoside, methyl D-glucoside, melibiose, inulin, D-raffinose, xylitol, D-lyxose, D-tagatose, D- and L-fucose, D-arabitol and L-arabitol.

Vitamin Requirements:

Stimulation of the growth of the bacterial strain is observed with thiamin, D,L-biotin and purine and pyrimidine bases. In contrast, no significant effect appears with vitamin B12, pyridoxine, nicotinic acid, p-aminobenzoic acid, Ca D-pantothenate, folic acid and riboflavin.

Genetic Characteristics:

The strain DKP is characterized by a content of guanine + cytosine, determined by HPLC by the method of Meshbah et al. (3), of 38.8±0.2%.

c. ANALYTICAL TECHNIQUES

The bacterial growth is monitored by measuring the increase in turbidity at 600 nm in Hungate tubes for anaerobic cultures with a Shimadzu UV 160A spectrophotometer.

The fermentation profile is determined using the base medium, to which are added, under sterile conditions, the carbohydrate tested, up to a final concentration of 0.3% (w/v), and 0.017% bromothymol blue. Two duplicate successive cultures are carried out for each carbohydrate, sterilized separately by filtration.

The vitamin requirements are determined using a chemically defined medium devoid of vitamins, supplemented with glucose up to a final concentration of 0.3% (w/v).

The vitamins and purine and pyrimidine bases are added under sterile conditions up to a final concentration of: nicotinic acid, thiamin HCl, Ca D-pantothenate, riboflavin, 992 µg/l; p-aminobenzoic acid, 551 µg/l; pyridoxine, 1,984 µg/l; vitamin B12, 1 µg/l; D,L-biotin, 10 µg/l; folic acid, 1 µg/l; adenine, guanine, uracil, xanthine, 5,157 µg/l. Bacterial suspensions which have been washed twice in sterile physiological solution containing 9 o/oo NaCl are used for the inoculations. Three successive culture are carried out for each vitamin.

Resistance forms (spores) were investigated by observation under a microscope and by culture of the strain after pasteurization at 80° C. for 20 minutes.

The temperature range for growth was defined in tube cultures incubated in water-baths regulated at various temperature.

The catalase activity is tested with a 3% (v/v) solution of hydrogen peroxide. The production of indole and ammonium are determined with Kovacs and Nessler's reagents respectively. Griess reagent is used to detect the reduction of nitrates.

$H_2S$ is measured by photometry as colloidal CuS after reaction with a mixture comprising 50 mM HCl and 50 mM $CuSO_4$.

Glucose, lactate, acetate, ethanol and formate are determined on diluted samples by HPLC using an Analprep 93 pump and a column of the type ORH 801. A flow rate of 0.6 ml/min, an injection loop volume of 20 µl and a column temperature of 35° C. are used. The detector used is a differential refractometer (Knauer, Berlin, FRG).

The amount of hydrogen is determined with the aid of a Girdel series 30 gas chromatograph equipped with a thermal conductivity detector. The column is packed with Carbosphere SS (mesh 60/80).

L(+)-Lactate and D(−)-lactate dehydrogenases are used to determined the stereoisomeric forms of the lactic acid produced by the fermentation of glucose (Boehringer Mannheim enzymatic kits). For analysis of the cytochromes, 3 g of the cells are subjected to sonar treatment in 10 ml of 20 mM Trishydrochloride buffer (pH 7.6); the suspension of crushed cells is centrifuged at 30,000 g for 45 min at 5° C. to remove the cell debris. The resulting supernatant is separated into a supernatant and a particulate fraction by centrifugation at 140,000 g for 2 h. The supernatant is regarded as the soluble fraction. The black gelatinous pellet is resuspended in the same buffer and represents the particulate fraction. Examination of extracts devoid of cells for cytochromes is carried out with the aid of a Shimadzu spectrophotometer, model UV 300.

d. CULTURE PROCESSES AND USES

1 PRODUCTION OF BIOMASS

For production of the biomass, two culture techniques are used:

1. In a non-renewed medium.

The fermentation is regulated at a pH of 7 with the aid of an alkaline solution (for example sodium carbonate) and at a temperature of 50° C. A culture medium corresponding to the following composition is used:

| | |
|---|---|
| Glucose | to be calculated |
| Yeast extract/protein hydrolysate | to be calculated |
| $NH_4Cl$ | 3 g/l |
| $KH_2PO_4$ | 3 g/l |
| $MgCl_2.6H_2O$ | 0.4 g/l |
| $FeSO_4.7H_2O$ | 5 mg/l |
| Tween 80 | 5 g/l |

The concentration of glucose and of growth factors is a function of the concentration of cells required. The following relationship can be used to estimate the concentration in the biomass at the end of fermentation:

$$1/X = 2.07/F + 3.78/G$$

X is the cell concentration in g/l (dry weight of the cells per litre)

G is the concentration of glucose in g/l

F represents growth factors contained in a mixture made up of 50% yeast extract and 50% of a protein hydrolysate (for example casein hydrolysed by trypsin), F being the concentration in g/l of the mixture.

The above relationship has been verified for a concentration range of glucose and growth factors ranging, respectively, from 5 to 60 g/l and 1 to 30 g/l.

By way of example, to obtain 7.6 g of cells (dry weight), 60 g of glucose and 30 g of growth factors are used. Under the operating conditions described above, fermentation lasts about 7 to 9 hours, the final concentration of lactic acid represents about 40% by weight of the end products and the productivity for cells is 1 g/l.h.

2. In a renewed medium.

The culture is regulated at a pH of 7 and at a temperature of 50° C. The fermenter is fed continuously with the above culture medium, in which the concentrations of growth factors (F) and of glucose depend on the concentration of cells required. To produce the biomass, it is advisable to choose a dilution level of 1 $h^{-1}$, with the energy source (glucose or other carbohydrates) as the nutritional factor which limits growth. Using glucose as the source of energy, it will be appropriate to choose a glucose/F ratio of about 0.75. The following two specified requirements will be used to calculate the concentrations of growth factors (F) and of glucose.

q F=6.6 g/g.h q G=3.5 g/g.h q F is the specific requirement of growth factors, expressed in g per g of cells (dry weight) and per hour.

q G is the specific requirement of glucose, expressed in g of glucose per g of cells (dry weight).

By way of example, using a culture medium in which the concentrations of glucose and of growth factors are 20 and 40 g/l respectively, and fixing the dilution level at 1 h$^{-1}$ (water retention time of 1 hour), a fermentation juice is obtained, in which the concentration of cells is 6 g/l (dry weight) with a cell productivity of 6 g per litre of fermenter and per hour. Under these conditions, the fermentation juice comprises about 2.5 g/l lactic acid, 5.5 g/l acetic acid, 4.2 g/l ethanol and 8.4 g/l formic acid.

2 Production of lactic acid

In a renewed medium.

The culture is regulated at a pH of 6 and at a temperature of 50° C. The fermenter is fed continuously with a culture medium in which the concentrations of growth factors (F) and of glucose depend on the concentration of cells required. To produce lactic acid, it is advisable to choose a dilution level of 0.4 h$^{-1}$, with growth factors F as limiting nutriments. Using glucose as the source of energy, it is appropriate to choose a glucose/F ratio of about 2. The following two specific requirements will be used to calculate the concentrations of growth factors (F) and of glucose.

q F=2.5 g/g.h q g=5 g/g.h q F is the specific requirement of growth factors, expressed in g (mixture made up of 50% yeast extract and 50% of a casein hydrolysate (casein hydrolysed by trypsin)) per g of cells (dry weight) and per hour.

q G is the specific requirement of glucose, expressed in g of glucose per g of cells (dry weight).

To calculate the concentration of lactic acid, a yield of the order of 80% with respect to the glucose consumed will be used.

By way of example, using a culture medium in which the concentrations of glucose and of growth factors are 63 and 31 g/l respectively, and fixing the dilution level at 0.4 h$^{-1}$ (water retention time of 2.5 hours), a fermentation juice is obtained, in which the concentration of cells is 5 g/l (dry weight) and the concentration of lactic acid is 50 g/l. Under these conditions, the productivity for lactic acid is 20 g per litre of fermenter and per hour.

BIBLIOGRAPHIC REFERENCES (1) Hungate et al. 1969, p. 117–132. In J. R. Norris and D. W. Ribbons (ed.), Methods in Microbiology. Vol. 3B. Academic Press, New York.

(2) Macy et al, 1972, Amer. J. Clin. Nutr. 26:1318–1323

(3) Meshbah et al, 1989, Int. J. Syst. Bacteriol. 39:159–167.

We claim:

1. An isolated bacterial strain deposited at C.N.C.M on Nov. 24, 1993 under No. I-1378.

2. An isolated *Bacillus thermoamylovorans* strain which is catalase positive, produces L(+)-lactate as a fermentation product and grows at a temperature in the range of 25° C. to 58.5° C., has an optimal growth of 47–53° C. and docs not reduce $NO_3^-$, wherein said strain is a *Bacillus thermoamylovorans* gen. nov. sp. nov.

3. The strain according to claim 2 wherein said strain is derived from palm wine.

4. The strain according to claim 2 wherein said strain has an optimum growth pH in the range of 6.8 to 7.2.

5. The strain according to claim 2 wherein said strain produces formate, acetate or ethanol.

6. A process for culturing the strain of claim 2 comprising anaerobic fermentation in a medium having a pH in the range of 5.4 to 8.5 comprising sugar which is utilized as a source of energy by said strain and a peptide which is utilized as a source of nitrogen by said strain.

7. The process according to claim 6 wherein said pH is in the range of 6.8 to 7.2.

8. The process according to claim 6 wherein said sugar is a carbohydrate and said peptide is a yeast extract or a protein hydrosylate.

9. A process for decontaminating industrial effluents comprising mixing said effluents with the strain of claim 2 such that said effluents are decontaminated.

10. A method of food production comprising fermenting the strain of claim 2 in the production of a food product.

11. A process for the production of at least one metabolite selected from L(+)-lactate, acetate, formate and ethanol, comprising culturing the strain of claim 2 such that said metabolite is produced, and recovering said metabolite.

12. The strain according to claim 2, said stain not containing cytochrome.

13. The isolated bacterial strain of claim 2 which is non-spore forming.

* * * * *